(12) United States Patent
Hillebrand et al.

(10) Patent No.: US 9,399,793 B2
(45) Date of Patent: Jul. 26, 2016

(54) DEVICE FOR DETECTING NUCLEIC ACIDS

(75) Inventors: Timo Hillebrand, Hoppegarten (DE); Claus Knippschild, Jena (DE); Elmara Graser, Berlin (DE)

(73) Assignee: AJ Innuscreen GmbH, Berlin (DE)

( * ) Notice: Subject to any disclaimer, the term of this patent is extended or adjusted under 35 U.S.C. 154(b) by 0 days.

(21) Appl. No.: 13/639,944

(22) PCT Filed: Apr. 8, 2011

(86) PCT No.: PCT/EP2011/055524
§ 371 (c)(1),
(2), (4) Date: Feb. 11, 2013

(87) PCT Pub. No.: WO2011/124688
PCT Pub. Date: Oct. 13, 2011

(65) Prior Publication Data
US 2013/0157348 A1    Jun. 20, 2013

(51) Int. Cl.
*C12Q 1/68*    (2006.01)
*B01L 3/00*    (2006.01)
*B01L 7/00*    (2006.01)

(52) U.S. Cl.
CPC .......... *C12Q 1/68* (2013.01); *B01L 3/5027* (2013.01); *B01L 7/52* (2013.01); *B01L 2300/0816* (2013.01); *B01L 2300/0825* (2013.01); *B01L 2300/0854* (2013.01); *B01L 2300/1822* (2013.01); *B01L 2300/1827* (2013.01); *B01L 2400/0481* (2013.01); *B01L 2400/0655* (2013.01)

(58) Field of Classification Search
CPC ........ B01L 2300/0816; B01L 2300/0825; B01L 2300/0854; B01L 2300/1822; B01L 2300/1827; B01L 2400/0481; B01L 2400/0655; B01L 3/5027; B01L 7/52; C12Q 1/68

USPC .......................... 435/283.1–309.4
See application file for complete search history.

(56) References Cited

U.S. PATENT DOCUMENTS

| 2004/0191896 | A1 | 9/2004 | Miao et al. |
| 2009/0023201 | A1 | 1/2009 | Hongo et al. |
| 2009/0053801 | A1 | 2/2009 | Miao et al. |
| 2010/0064781 | A1 | 3/2010 | Cherubini et al. |
| 2011/0039261 | A1 | 2/2011 | Hillebrand et al. |

FOREIGN PATENT DOCUMENTS

| DE | 10 2006 036 171 | 10/2008 |
| DE | 10 2007 062 441 | 6/2009 |
| EP | 2 071 026 | 6/2009 |
| EP | 2 163 306 | 3/2010 |
| WO | 97 27324 | 7/1997 |

OTHER PUBLICATIONS

International Search Report Issued Aug. 4, 2011 in PCT/EP11/55524 filed Apr. 8, 2011.

*Primary Examiner* — Nathan Bowers
*Assistant Examiner* — Lydia Edwards
(74) *Attorney, Agent, or Firm* — Oblon, McClelland, Maier & Neustadt, L.L.P.

(57) ABSTRACT

The invention relates to a device that allows a target nucleic acid to be detected in a homogeneous batch using two different detection formats. The device comprises at least two heatable sample blocks and a reaction cartridge which contains a base (1, 15) and at least one film (3, 4) sealing the base (1, 15), wherein the film (3, 4) comprises a surface (13, 14) that is not connected to the base (1, 15) and said surface (13, 14) forms a volume (16) for media transfer or at least one reaction chamber (10). The device can be used in particular for mobile gene diagnostics under field conditions.

10 Claims, 3 Drawing Sheets

DEVICE FOR DETECTING NUCLEIC ACIDS

The subject matter of the invention is a device with which a target nucleic acid in a homogeneous batch can be detected with two different detection formats. The device may be used in particular for mobile gene diagnostics under field conditions.

PRIOR ART

The investigation of diagnostically relevant biological samples such as serum, plasma, blood, swab samples or organ grit for detection of infectious pathogens has increased enormously in importance in recent years. Virus infections such as HIV, HCV or HBV are spreading worldwide. Furthermore, bacterial infections are also spreading once again, among other reasons as the result of incipient climatic changes. The emergence of new infectious diseases with fatal outcome and an extremely high infection potential (SARS, bird flu) is proving ever more clearly that a rapid diagnosis capable of being performed on the spot will be decisive for preventing epidemics. Furthermore, diagnostic systems that are easy to handle and relatively inexpensive, especially in developing countries, will also play a significant role in fighting the spread of infectious diseases. The tests used at present, especially for the detection of viral infectious diseases (HIV, HCV, HBV, dengue fever and many others) are based mostly on performing REAL-TIME PCRs. These tests are dependent on extremely expensive instrumental prerequisites as well as on expensive reagents. Such methods can be performed only by trained specialized personnel in special-purpose laboratories.

A further main aspect relates to the performance of diagnostic tests aimed at early detection of terrorist attacks (smallpox, plague, anthrax). It is extremely important to find an exact result in precisely these fields of application, because numerous far-reaching response actions for protection of the population are initiated on the basis of such results. Diagnostic tests in use at present (some of which can also be performed on the spot) therefore always need a confirmatory investigation on a second detection platform (for example, first diagnosis of the pathogen by means of real-time PCR and confirmation of the diagnostic result by applying the amplification preparation on an agarose gel). In this context, effective fast on-the-spot detection is not entirely necessary, since the confirmatory investigation on a second detection platform is not a part of currently existing system solutions (for example, mobile LightCycler detection does not offer the capability of second confirmatory detection).

U.S. Pat. No. 6,565,815 B1 falls within the prior art. The optical unit (detection unit) described in this document provides light entry that takes place laterally from underneath, in a manner separated spatially from the heating unit. Reaction monitoring in this system takes place only by optical means. Further product monitoring, such as immunological detection by means of lateral-flow strips, is not provided. The structure of the cartridge (consumable) comprises light-reflecting walls as well as mounted optical lenses. In this system several materials are used for manufacture of the reaction chamber. The beam path passes through two optical windows, disposed at an angle of 90° relative to one another, in the reaction chamber. An absorption measurement is not possible in this system, since it is not possible to define the length of the beam path. The contact pressure of the sample blocks in U.S. Pat. No. 6,565,815 B1 is not achieved by means of a helical spring. The optical unit is not adjusted directly on the sample block.

The document DE 102006036171 A1 also falls within the prior art. Therein there is described an arrangement and a method for quick PCR with multi-channel fluorescence measurement. The described apparatus is designed especially for 96-well MTPs (micro titer plates). The reaction space in DE 102006036171 A1 is not defined by the heating elements but instead is predetermined by the MTP. By virtue of the layer thickness of the cavity wall, powerful heating elements (thermal efficiency) are indispensable and therefore constitute an obstacle to miniaturization or mobility (voltage supply). The heating elements are located underneath the cavities, or else above them (top heating). The reaction space is not oriented perpendicular to the sample blocks. Light entry takes place from above (not laterally) and not directly into the sample but instead into the cavity, which contains an undefined volume of air in the head space. Furthermore, the light is passed both into and out of the sample via the same optical fiber. An absorption measurement is not possible, because of the undefined path length of the light. Because of the relatively long light path in the sample and the cavities of unequal size, optical lenses are also necessary. The described arrangement does not represent a suitable product for operation "in the field" (also because of its multi-channel fluorescence measurement and the lack of an internal voltage source).

The objective of the present invention was therefore to provide a detection system that is simple to use (even by non-specialists), quickly yields a diagnostic result and can also be used on the spot. The detection system is intended to permit two detection options to be achieved in order to verify the first diagnostic result.

In publications DE 102007062441 A1 and WO 2009/080817 A2 there are described instrumental systems that permit mobile nucleic acid isolation from any desired complex biological samples as well as mobile detection of nucleic acids on the spot. These instrumental systems have now become available on the market and permit the achievement of nucleic acid isolation followed by detection of specific nucleic acids.

The core component of the detection unit is a reaction cartridge, which when loaded with amplification reagents and sample nucleic acids to be investigated permits the achievement of an extremely fast amplification reaction. The specific target nucleic acids are then detected by transferring the amplified reaction batch onto a downstream lateral-flow test strip. Final colorimetric detection (FIG. 5) takes place on the test strip. The entire system is optionally battery-powered and can therefore be used under field conditions.

The detection reaction taking place on the test strip is also disclosed in publications DE 102007062441 A1 and WO 2009/080817 A2. It is a combination of an amplification and hybridization reaction followed by detection of the product on an immunological test strip.

The inventive method is based on the use of the instrumental systems disclosed in the above-mentioned publications and it represents a significantly improved variant.

Surprisingly, it has been found that it is possible to achieve dual detection of a target nucleic acid in an improved reaction cartridge and therefore also to use such a test system in battery-powered mode under field conditions. With the inventive dual test system, it is possible for the first time to verify a diagnostic result by means of a second test format even under field conditions. A further important advantage is achieved in this system by the fact that both tests are able to run in a novel reaction cartridge and that the reaction cartridge permits a homogeneous test procedure for both detection reactions, meaning that both detection reactions taken place in such a way that the reaction cartridge does not have to be opened at any time. This represents an enormous advantage, since amplification products therefore never come into contact with the environment and so contamination risks do not transpire (in contrast, contamination risks after LightCycler detection, for example, are possible if the amplification product is subsequently applied and separated on an agarose gel for confirmation).

The inventive reaction cartridge advantageously consists of a base body and at least one film, which seals the base body and has at least one face not joined to the base body (FIG. 1 and FIG. 6: Section through reaction space with films). The face of the film not joined to the base carrier is then able to form a reaction chamber (FIG. 1). Furthermore, a face not joined to the base carrier can be used for volume transport (FIG. 6). The non-joined faces can therefore form several volumes together with the base body, for example forming two reaction chambers and being usable for volume transport. Thus a first reaction chamber is used for the inventive optical detection, and the second reaction chamber permits immunological detection.

For this purpose the second reaction chamber contains a lateral-flow test strip. The inventive reaction cartridge therefore achieves, for the first time, dual detection on two different detection principles and in this way permits a second, independent verification reaction.

The combination of the two detection formats is achieved as follows according to the invention.

The inventive dual detection method is based on a matrix-dependent DNA de novo synthesis with a hybridization step. The inventive choice of labels on the oligonucleotides participating in the reactions permits both reaction-dependent fluorescence measurement and associated numerical and possibly quantitative evaluation (optical detection) as well as subsequent immunological detection in the form of visualization of the reaction, for example on a lateral-flow strip.

According to the invention, the sample blocks are disposed one upon the other when the cartridge is not inserted. The contact pressure of the sample blocks is applied by means of a helical spring. The optical unit is not adjusted directly on the sample block. The direct mounting of the optical fiber in the sample block guarantees a minimum path of the light after it exits the fiber and passes into the sample (minimization of scattering and refraction effects). It is therefore not possible to insert/operate the inventive consumable in the device described in the document U.S. Pat. No. 6,565,815 B1 and vice versa. For optimum heat transfer into the sample, some contact pressure between the films of the reaction chamber and the sample block is necessary. This is achieved according to the invention by the pressing force and form-fitting relationship of the sample blocks with the reaction chamber and the resulting sealing of the sample chamber (clamping of the injection channel). The advantages of the convexly shaped sample blocks according to the invention are also apparent in this system.

The inventive device also differs clearly from that described in DE 102006036171 A1. The main difference in this case consists in the distance of the fibers from the sample. In DE 102006036171 A1, the light must first travel through the sealing film of the samples and then the headspace above the sample before it passes into the sample. This in turn leads to considerable scattering and refraction effects, which do not occur in the inventive arrangement.

The inventive method of dual detection in the present system proceeds in the following steps:

A. Supplying a Reaction Batch, Consisting of:
 a sample containing a nucleic acid, in which the target nucleic acid is to be detected
 at least one oligonucleotide marked with a label 1, which is completely or partly complementary to the target sequence and functions as a primer in a matrix-dependent de novo synthesis of the target nucleic acid (oligo type 1)
 at least one oligonucleotide marked with a label 2, which by virtue of the lower melting temperature than that of oligonucleotide 1 does not participate in the DNA de novo synthesis process, but is able to hybridize partly or completely with the DNA de novo synthesis product of oligo type 1 (oligo type 2)
 a mixture of chemicals/enzymes, possibly also with further unlabeled oligonucleotides, for permitting a matrix-dependent de novo synthesis of the target nucleic acid.

According to the invention, the labels of the two oligonucleotides (oligo type 1 and oligo type 2) are chosen such that together they form a FRET pair (such as FITC/TAMRA, FAM/TAMRA, FAM/BHQ1, etc.) and, in relation to the inventive dual detection, are also capable of having complementary binding partners on a lateral-flow strip.

B. Performing the Matrix-Dependent DNA De Novo Synthesis with Integrated Probe Hybridization Depending on the type of target nucleic acid, there is performed either a reverse transcriptase reaction (in the case of RNA, which occurs in a very large number of copies, such as rRNA, tmRNA) or amplification (DNA); it is even possible (in the case of a rare RNA, such as mRNA, samples with a small number of particles) to perform the two reactions in succession.

By virtue of the inventive method, only oligo type 1 participates in this first reaction. The oligo type 1 functions as a primer either in an RNA-dependent reverse transcription (whereby a labeled cDNA strand is formed) or in amplification of the target DNA or cDNA (whereby a labeled PCR product is formed). One-step RT-PCR can also be performed. In this process a second unlabeled primer oligonucleotide increases the PCR yield.

By virtue of its lower annealing temperature in accordance with the inventive method, the oligo type 2 does not participate in the DNA de novo synthesis. Thereafter the reaction batch is heated to a temperature of >90° C. This step leads to thermal separation of the strands. After the end of this denaturing reaction, the reaction batch is cooled to the hybridization temperature of oligo type 2. During this step, the oligo type 2 binds specifically to the complementary DNA strand. This strand then carries label 1, which was incorporated into the reaction product by the oligo type 1.

C. Dual Detection of the Hybridization Event

The detection reactions take place in succession in the same reaction cartridge.

1. Detection of the hybridization reaction by means of a fluorescence measurement, wherein the labels incorporated by the two oligos type 1 and type 2 form a FRET pair. The hybridization of the oligo type 2 with the synthesis product of the oligo type 1 that takes place in the inventive method leads to a FRET effect between labels 1 and 2. This effect now leads to a measurable decrease of the fluorescence. This reduction of the fluorescence is numerically evaluated, thus permitting unambiguous detection of the reaction. After optical detection has been achieved, the reaction batch is transferred into the second reaction chamber of the cartridge (which contains a lateral-flow strip) by addition of a run buffer, which was injected into the reaction cartridge. The reaction batch/run buffer is transferred via the face formed by the film that seals the base body of the reaction cartridge.
2. Detection of the hybridization reaction on the lateral-flow strip in the second reaction chamber of the inventive reaction cartridge.

The lateral-flow strip contains a binding site for one of the labels of oligo type 1 or type 2 and/or antibodies or other binding molecules against the labeling molecules of oligos type 1 or type 2 that are able to bind to the labeling molecules of type 1 or type 2 (for example, covalent bonds or hydrogen bonds or via bridging molecules). Furthermore, a detection molecule for visualization or measurement of the hybridization result is located on the solid phase, or such a detection molecule is added to the detection reaction. However, it is also possible to incorporate the detection molecule into the hybridization product to be detected as early as during the amplification/hybridization reaction.

It is then a simple matter to detect the immunological reaction on the test strip, for example visually.

Following the diagnosis, the reaction cartridge is discarded.

In summary, an extremely simple and universally usable detection method for gene diagnostics is now available with the inventive method.

According to the invention, the dual detection of a diagnostically relevant target nucleic acid to be detected takes place in the form of a homogeneous assay via the end-point fluorescence measurement of fluorescence quenching and subsequently via immunological detection on a lateral-flow strip. The result can be acquired numerically and it also permits detection and quantification of the target nucleic acid to be detected (using an internal standard). The inventive method of dual detection therefore achieves, in an elegant and extremely simple way, a first diagnostic detection of a target nucleic acid by means of fluorescence detection followed in the same reaction cartridge by verification of the result on a lateral-flow strip.

From the diagnostic viewpoint, such a verification is therefore very much more exact than the detection that has been possible heretofore of real-time PCR products on an agarose gel. The method can also be used under field conditions.

This elegant novel test procedure, and especially also the combined test procedure (fluorescence detection followed by verification of the first test reaction on a solid phase), are made possible according to the invention by the fact that the hybridized probe (oligo type 2) is not decomposed by the Taq polymerase during amplification and hybridization but instead remains in the hybridized condition even after the end of the reaction, in contrast to the homogeneous TaqMan exonuclease assay.

The inventive integration of a hybridization probe into the reaction provides the certainty that the amplified fragment actually contains the target sequence. Thereby false-positive results caused by mispriming are excluded. The use of the chemically modified probe (preferably phosphorylation of the last nucleotide of the probe) prevents the extension of the probe by 5'→3' polymerase activity and thus prevents the probe from functioning as a primer and generating unspecific PCR artifacts (primer dimers), which would be detected as false-positive signals.

In contrast to real-time PCR methods, the detection of the specific detection signal takes place not during amplification, where the fluorescence is released either due to the probe hydrolysis caused by the Taq polymerase (EP 0972848 A2) or is reduced by the FRET effect (EP 1384789 B1), but only after the end of the amplification-hybridization reaction. Such a method also would not permit subsequent immunological detection on a lateral-flow test strip.

The inventive method also differs from the patent (EP 0826066 B1) that also describes a combination of PCR and hybridization. In this method also, a FRET-effect-mediated fluorescence signal is again detected. This occurs during the process of amplification by hybridization of a doubly labeled probe having a lower annealing temperature than that of the primer. The release of fluorescence in this case takes place not by hydrolysis of the probe as a result of the exonuclease activity of the polymerase but instead by the fact that the secondary structure of the probe is loosened during hybridization and fluorescence is released by removal of the reporter from the quencher. In this case only enzymes having no exonuclease activity (e.g. Klenow fragments or T4 or T7 polymerases) can be used for amplification.

As already explained, the inventive method can also be performed under field conditions. The instrumental basis has already been disclosed in publications DE 102007062441 A1 and WO 2009/080817 A2. The inventive novel method of dual detection and the reaction cartridge improved according to the invention are further characterized in that they permit PCR to be achieved quickly inside the reaction tubes, in a process known as rapid PCR. In this form of PCR large amounts of energy must be input very rapidly into a reaction tube or reaction space, in order to achieve very rapid temperature changes (up to 15° C./s).

For standard consumables or vessels, this requires the use of very powerful heating elements (Peltier elements, heating films, etc.) which, because of their power consumption, are incompatible with mobile service owing to the needed limiting batteries or accumulators.

In order to circumvent this problem, for example in existing chip solutions, the volume to be heated is very greatly reduced (volume <1 µL to nL), so that only a very small volume has to be heated here. Under these circumstances, however, the ability to manipulate such a volume is completely disregarded. Furthermore, considerable evaporation problems are encountered here with such a volume.

Surprisingly, it was already shown in the first tests during use of the inventive cartridge that an extremely high heating rate can be achieved even in a large volume (25 µL) with the use of commercial standard Peltier elements. This was achieved by using the sealing films on the base body. These films can be chosen—without causing any loss of stability of the overall cartridge—in minimum thicknesses (<100 µm).

The sealing films together with the base body form a reaction space that can be filled with the reaction batch. In order to achieve the needed heat input into the reaction volume, 2 sample blocks (from each side of a FIG. 2) are pressed onto the reaction space with large force (e.g. >60 N each). These sample blocks have a shape slightly convex into the sample block, thus sealing it hermetically by the shape and the large force. The force exerted on the sample blocks can be chosen to be very high, since the sealing film becomes only slightly convex and is not destroyed even at minimum thickness of the film.

Because of the convexity of the sample blocks, a slightly constricted place is formed in the middle of the reaction chamber. The problem of air bubbles forming in the sample liquid is solved by the vertical arrangement of the cartridge, since the air bubbles form an air-filled space in the upper part of the reaction chamber. This problem is also found in many state-of-the-art systems, and in some cases is prevented by very complex means (air bubbles in the sample liquid). In the inventive arrangement of the cartridge, this developing air-filled space even acts positively. Surprisingly, it has been found during determination of the heating rates that the pressure in the vessel rises (expansion of the air) when an air space has formed. The rising pressure at high temperatures (e.g. 90° C.) ensures that the film is pressed against the sample blocks for even better heat transmission, thus further improving the heat transfer. This effect can be utilized for this consumable, but is not crucial to the inventive use.

In the inventive instrumental configuration, an optical detection unit is now included as an expansion of the disclosed instrumental systems of the above-mentioned publications.

The optical detection permits the described measurement of the fluorescence for the first detection reaction in the first reaction chamber of the reaction cartridge.

Once the sample blocks have been pressed into place, the distance of the sealing films from one another is dictated by the thickness of the base body and the geometry of the sample blocks. This reproducible distance between the sample blocks was found in test measurements to be a very good basis for optical detection inside a reaction chamber. Thus an optical path length is defined merely by the thickness of the consumable (assuming constant arrangement of the sample blocks). This effect makes it possible to perform an absorption measurement that is reproducible from one sample block to the other, for example in order be able to achieve detection via a DNA concentration (see FIG. 3 and FIG. 4, reaction chamber with optical detection or arrangements for fluorescence detection and measurement of absorption by the reaction chamber). For this purpose, light is input (through the sealing film) into the cartridge (e.g. via optical fibers) at one sample block and output to a detector through the sealing film (e.g. also via an optical fiber) in the other sample block. For this purpose the sealing films are chosen such that they correspond to the optical requirements of the detection method (e.g. little absorption of the light by the sealing films/the sealing films must be transparent for wavelengths of the detection principle).

While a cartridge is not in use, the sample blocks do not bear upon one another directly with their convexity, and the pressing force can be achieved, for example, by a spring mechanism or a simple mechanical structure. If a cartridge with a different thickness of the base body is now used, the optical path length is influenced but not the amplification of the sample by the rapid PCR. The heat transfer through the sealing films makes a complicated regulation system for temperature control superfluous, since the temperature in the sample blocks corresponds to that in the cartridge with almost 100% precision. Thus the volume in the reaction chamber and the optical path length can be positively influenced by the change in thickness of the base carrier.

Likewise it is possible to guide an exciting wavelength in one sample block (e.g. via at least one optical fiber) into the cartridge and to output the fluorescence response of the sample to a detector (see FIG. 3: Reaction chamber with optical detection or arrangements for fluorescence detection) via the identical fiber (or a second fiber, also located in the same sample block or in the 2nd sample block).

The arrangement also makes it possible to combine both detections in one arrangement, by designing both sample blocks for absorption and fluorescence detection (see also reaction chamber with optical detection or arrangements for fluorescence detection and measurement of absorption by the reaction chambers).

Thus, by virtue of the combination of the inventive method for dual detection of a target nucleic acid with the inventive device, a test system that permits an initial diagnostic result to be confirmed by a second diagnostic test result even under field conditions is available for the first time. In this way the certainty of a diagnostic estimate can be significantly improved.

The inventive cartridge consists of at least one base body, at least one film that seals it and has at least one face not joined to the base body, which face forms, together with the base body, at least one volume for media transfer and/or at least one reaction chamber.

The at least one formed reaction chamber has the following advantages:
  The detection of one or more targets is possible
  Optical detection of an amplification of one or more targets can be achieved
  Detection of one or more targets by means of a test strip can be achieved
  In each case different detection methods for one or more targets can be performed.
  2 different detection methods are possible

FIGURE LEGENDS

Figure 1:
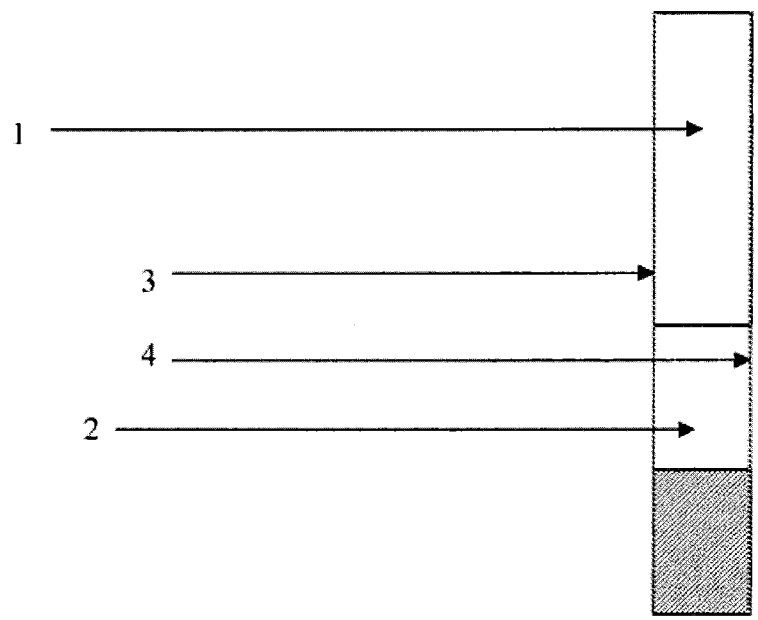
FIG. 1 shows a section through the reaction space with films.
Figure 2:
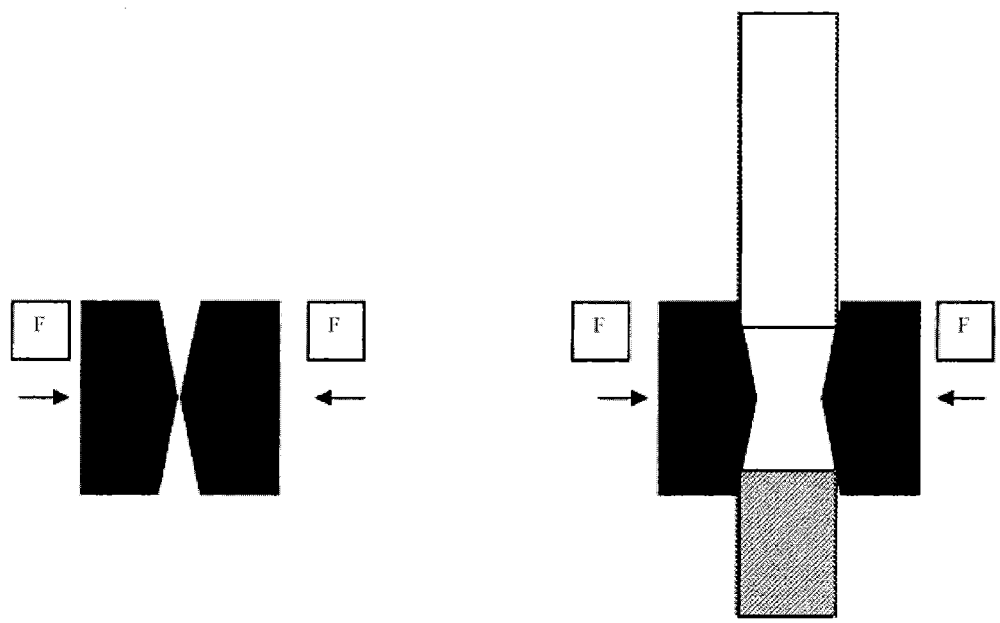
FIG. 2 shows a section through the reaction chamber with sample blocks as well as sample blocks without reaction chamber.
Figure 3:
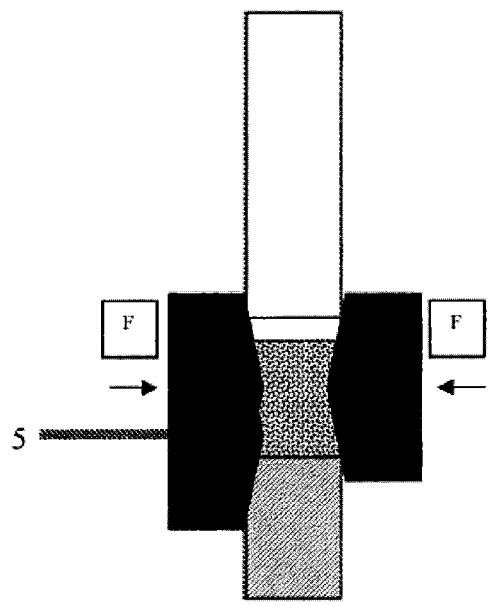
FIG. 3 shows the reaction chambers with optical detection or arrangements for fluorescence detection.
Figure 4:
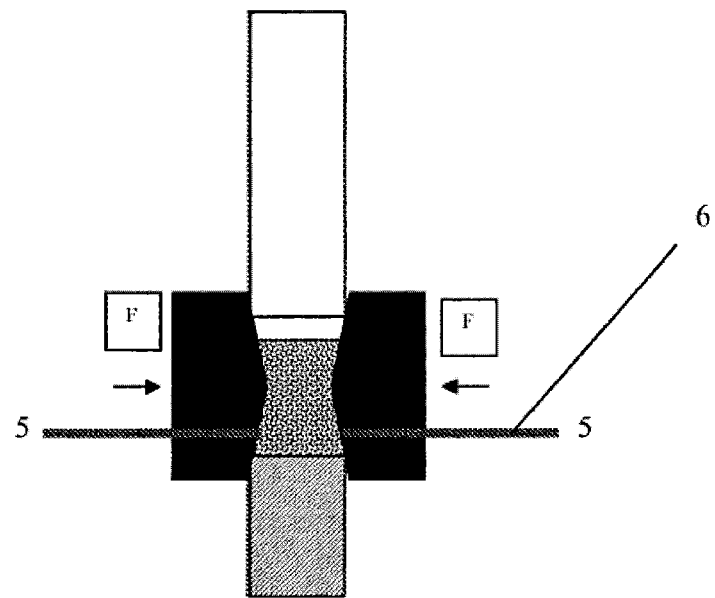

The reaction chambers with optical detection or arrangements for fluorescence detection and measurement of absorption by the reaction chamber are illustrated in FIG. 4.

Figure 5:
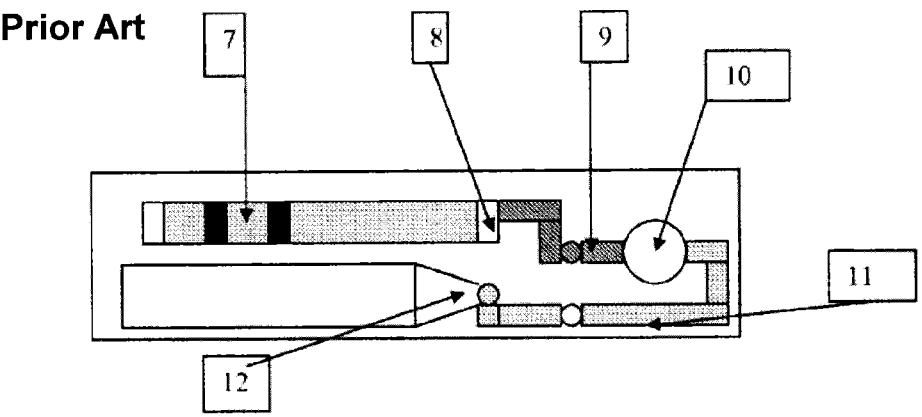

FIG. 5 shows the basic arrangement of the reaction cartridge.

Figure 6:
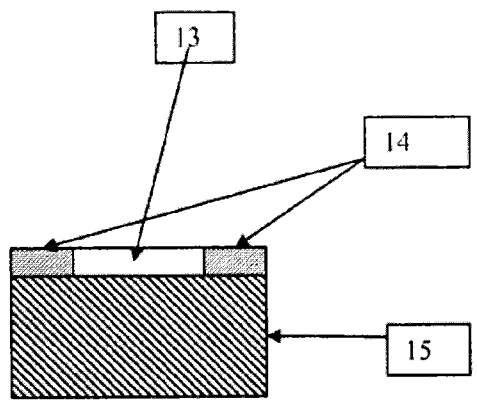

FIG. 6 shows the structure of film faces not joined to the base body for volume transfer (diagram without volume transfer).

Figure 7:
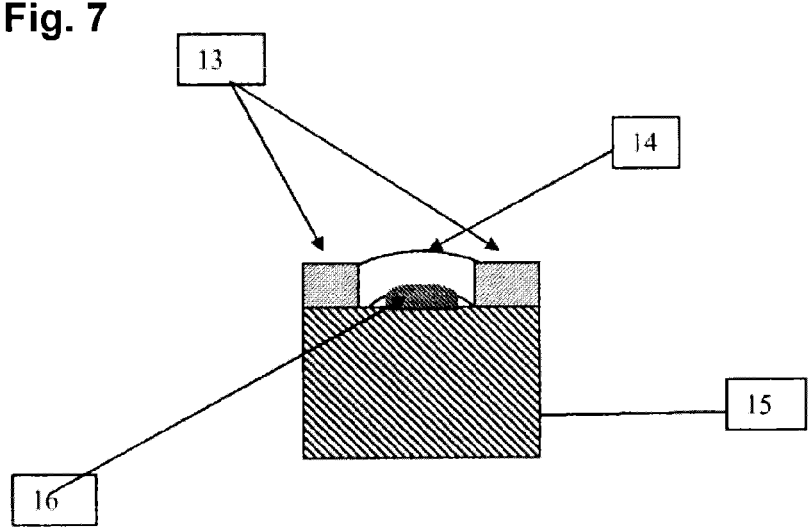

FIG. 7 shows the structure of film faces not joined to the base body for volume transfer (diagram with volume transfer). Reference numeral 16 shows the volume transfer to the base carried through the non-joined face of the face (if liquid under pressure is forced into the non-joined face, the film becomes convex and volume transfer is permitted).

LIST OF REFERENCE NUMERALS

The Reference Numerals Mean:

| | |
|---|---|
| 1 | Base body |
| 2 | Reaction volume |
| 3 | Sealing film 1 |
| 4 | Sealing film 2 |
| 5 | Optical structural element/light source and/or detector |
| 6 | Optical fiber |
| 7 | Test strip (lateral flow stripe) |
| 8 | Chamber for test strips |
| 9 | Flow channel to the chamber with test strip |
| 10 | Reaction chamber |
| 11 | Flow channel to the reaction chamber |
| 12 | Inlet aperture for inflow of media |
| 13 | Non-joined face of the film with the base body |
| 14 | Joined face of the film with the base body |
| 15 | Base body |
| 16 | Volume transfer |

The invention claimed is:
1. A device for detecting nucleic acids, comprising:
a reaction cartridge holder; and
a reaction cartridge configured for insertion into the reaction cartridge holder;
wherein
the cartridge holder comprises at least two sample blocks having heating elements and at least one optical detection unit, the reaction cartridge, comprises:

a base body;

a film sealed to edges of the base body such that a face of the film within the edges is not sealed to the base body and is capable to form a volume for media transfer and reaction chambers; and an injection channel;

wherein the reaction cartridge inserts into the reaction cartridge holder such that the two sample blocks contact and exert pressure on the film of the reaction cartridge at a first reaction chamber such that the inserted cartridge is sealed at the injection channel and the cartridge comprises the first reaction chamber and a second reaction chamber, and the second reaction chamber is located in a reaction flow succession following the first reaction chamber and comprises a lateral-flow test strip.

2. The device according to claim 1, wherein the sample blocks have a convexity such that when the reaction cartridge is inserted into the reaction cartridge holder a constriction is formed at the first reaction chamber.

3. The device according to claim 1, wherein a thickness of the film is less than 100 μm.

4. The device according to claim 1, wherein the reaction cartridge is perpendicular to the sample blocks.

5. The device according to claim 1, wherein a distance of the sealing films from one another after the sample blocks have been pressed into place is dictated by the thickness of the base body and the geometry of the sample blocks.

6. The device according to claim 1, wherein the sample blocks do not bear upon one another directly with their convexity while a cartridge is not inserted, and the pressure exerted by the sample blocks is achieved by a spring mechanism.

7. The device according to claim 1, wherein the optical detection unit comprises:

an optical fiber for input of light through the sealing film of the first reaction chamber on one sample block; and an optical fiber output to a detector in the other sample block.

8. The device according to claim 7, wherein the instrument inputs an exciting wavelength through an optical fiber to a sample in the reaction chamber and a fluorescence response of the sample is registered in a detector via the optical fiber or a 2nd fiber, wherein the detector is in the same sample block or another sample block.

9. The device according to claim 1, wherein the two sample blocks are forced onto the film at the reaction space with a force of at least 5 N.

10. A device for detecting nucleic acids, comprising:

a reaction cartridge holder; and a reaction cartridge configured for insertion into the reaction cartridge holder;

wherein the cartridge holder comprises at least two sample blocks having heating elements and at least one optical detection unit, the reaction cartridge, comprises:

a base body;

a film sealed to edges of the base body such that a face of the film within the edges is not sealed to the base body and is capable to form a volume for media transfer and reaction chambers; and an injection channel;

wherein the reaction cartridge inserts into the reaction cartridge holder such that the two sample blocks contact and exert pressure on the film of the reaction cartridge at a first reaction chamber such that the inserted cartridge is sealed at the injection channel and the cartridge comprises the first reaction chamber and a second reaction chamber, and the second reaction chamber is located in a reaction flow succession following the first reaction chamber and comprises a lateral-flow test strip;

wherein said device achieves dual detection of a target nucleic acid without opening of said reaction cartridge and wherein said device is battery-powered.

* * * * *